United States Patent [19]

Vorbruggen

[11] 4,090,021
[45] * May 16, 1978

[54] PROCESS FOR THE PRODUCTION OF N⁶-SUBSTITUTED ADENOSINE NUCLEOTIDES AND PRODUCTS RESULTING THEREFROM

[75] Inventor: Helmut Vorbruggen, Berlin, Germany

[73] Assignee: Schering Aktiengesellschaft, Berlin and Bergkamen, Germany

[*] Notice: The portion of the term of this patent subsequent to Sep. 28, 1993, has been disclaimed.

[21] Appl. No.: 608,250

[22] Filed: Aug. 27, 1975

Related U.S. Application Data

[63] Continuation-in-part of Ser. No. 295,719, Oct. 6, 1972, Pat. No. 3,983,104.

[30] Foreign Application Priority Data

Oct. 8, 1971   Germany ............................ 2151013

[51] Int. Cl.² ............................................ C07H 19/20
[52] U.S. Cl. ...................................... 536/28; 424/180; 536/24
[58] Field of Search ................... 260/211.5 R; 536/24, 536/27, 28, 29

[56] References Cited

U.S. PATENT DOCUMENTS

| | | | |
|---|---|---|---|
| 3,208,997 | 9/1965 | Iwai et al. | 260/211.5 R |
| 3,225,029 | 12/1965 | Yamaoka | 260/211.5 R |
| 3,298,923 | 1/1967 | Banno et al. | 260/211.5 R |
| 3,413,283 | 11/1968 | Nomura et al. | 260/211.5 R |
| 3,590,029 | 6/1971 | Koch et al. | 260/211.5 R |
| 3,708,469 | 1/1973 | Vorbruggen et al. | 260/211.5 R |
| 3,891,623 | 6/1975 | Vorbruggen et al. | 260/211.5 R |
| 3,983,104 | 9/1976 | Vorbruggen | 536/24 |

*Primary Examiner*—Johnnie R. Brown
*Attorney, Agent, or Firm*—Millen & White

[57] ABSTRACT

N⁶-substituted adenosines of the formula

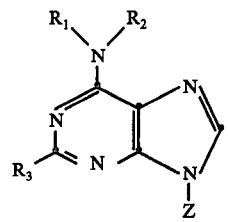

wherein $R_1$ and $R_2$ each are a hydrogen atom or an alkyl, aralkyl, aryl or heterocyclic ring, or $R_1$ is a hydrogen atom and $R_2$ is hydroxy, amino, alkyl terminally substituted, or $R_1$ and $R_2$ collectively with the nitrogen atom are a heterocyclic ring; $R_3$ is a hydrogen atom, amino or silylated amino; and Z is a phosphoric acid esterified sugar radical; possess antiproliferative activity and have beneficial effects upon the cardiovascular system; are produced by reacting a 6-trialkylsilyloxy purine of the formula

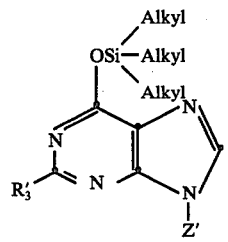

wherein each alkyl are alike; $R_3'$ is a hydrogen atom or trialkyl silylamine; and Z' is a sugar radical blocked with a phosphoric acid ester group, with ammonia or a primary or secondary amine, or with a corresponding salt of the amine, employing the amine salt or a Lewis acid as reaction catalyst.

13 Claims, No Drawings

PROCESS FOR THE PRODUCTION OF N⁶-SUBSTITUTED ADENOSINE NUCLEOTIDES AND PRODUCTS RESULTING THEREFROM

BACKGROUND OF THE INVENTION

This is a continuation-in-part of application Ser. No. 295,719, filed Oct. 6, 1972, now U.S. Pat. No. 3,983,104.

This invention relates to a process for the production of N⁶-substituted adenosines of the general Formula I

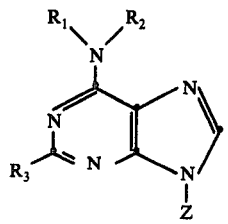

wherein $R_1$ and $R_2$, which can be alike or different, each are hydrogen, alkyl, e.g., of 1–6 carbon atoms, aralkyl or aryl, e.g., monocyclic carbocyclic aryl of up to 10 carbon atoms and unsubstituted or substituted, e.g., by hydroxy or alkoxy of 1–4 carbon atoms, or a heterocyclic ring, e.g., of 4–7 members and as hetero atoms 1–3 of N, S and O, or $R_1$ is a hydrogen atom and $R_2$ is hydroxy, amino, alkyl substituted on the terminal carbon atom, or $R_1$ and $R_2$ collectively with the N-atom are a heterocyclic ring preferably of 4, 5, 6, or 7 ring members and preferably containing a total of 1–3 hetero atoms, e.g., nitrogen, oxygen and/or sulfur; $R_3$ is a hydrogen atom or a free or silylated amino, e.g., trialkylsilylamino; and Z is a free or blocked sugar radical.

In the process of Ser. No. 295,719 for producing such compounds, whose disclosure is incorporated by reference, a 6-trialkyl-silyloxypurine derivative of general Formula II

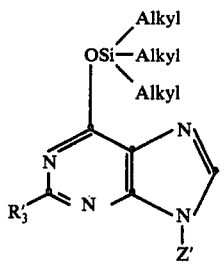

wherein each alkyl is alike and is lower alkyl, e.g., of 1–4 carbon atoms, preferably methyl; $R'_3$ is a hydrogen atom or trialkylsilylamino; and Z′ is a blocked sugar radical, viz., a silylated sugar radical, an acylated sugar radical or a sugar radical blocked by an acetal group, is reacted with ammonia or an amine of the formula $HNR_1R_2$ wherein $R_1$ and $R_2$ have the values given above, or a salt of the amine, optionally employing the amine salt or a salt of a Lewis acid as a reaction catalyst, and optionally thereafter the blocking groups on the sugar radical are removed.

Especially suitable as the sugar blocking groups in the process of Ser. No. 295,719 are trimethylsilyl groups, because they can be easily removed. The starting compounds of general Formula II which are silylated on the sugar radical are obtained by reacting free adenosine or guanosine with, for example, hexamethyldisilazane (HMDS) in the presence of trimethylchlorosilane or ammonium salts and optionally in the presence of a tertiary base, such as pyridine. The 6-trimethylsilyloxy group and the blocking trimethylsilyl groups are simultaneously introduced.

SUMMARY OF THE INVENTION

In a process aspect, this invention relates to a method for conducting the process of Ser. No. 295,719 employing as starting compound a compound of general Formula II wherein Z′ is a sugar moiety at least one of whose hydroxy groups is blocked by a phosphoric acid ester group and all other free hydroxy groups thereof, including those of the phosphoric acid ester group, are silylated.

In composition aspects, this invention relates to novel starting compounds for and products of the process of this invention.

DETAILED DISCUSSION

The starting compounds of Formula II are produced by silylating a 6-hydroxypurine of general Formula III

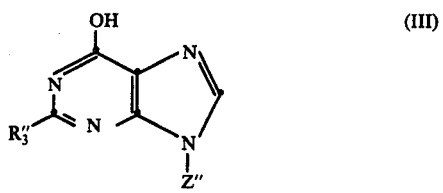

wherein $R''_3$ is a hydrogen atom or an amino group and Z″ is an acylated sugar moiety wherein the acyl group or groups are those of phosphoric acid, i.e., Z″ is a sugar moiety at least one of whose hydroxy groups is blocked by a phosphoric acid ester group, e.g., compounds otherwise corresponding to those of Formulae Ia, IV and V but having a 6-OH group instead of a 6-$NR_1R_2$ group.

The phosphoric acid can be linked to the sugar moiety Z′ and Z″ of the starting compounds of Formulae II and III and Z of the products of Formula I by either one or two hydroxy groups of the sugar moiety. When the linkage is effected by two hydroxy groups, these can be two hydroxy groups on one molecule or on one hydroxy group on each of two molecules, i.e., Z′ can be a sugar radical at least one of whose hydroxy groups, usually the primary hydroxy group, is acylated with a $(HO)_2$—P(O)—group or with a —P(OH)(O)—group bridging another, like acylated molecule, or two of whose hydroxy groups are acylated with a —P(OH)(O)—group to form a cyclic ester.

When only one hydroxy group of a single molecule is blocked, the product is a monophosphoric acid ester, e.g., of the general Formula Ia

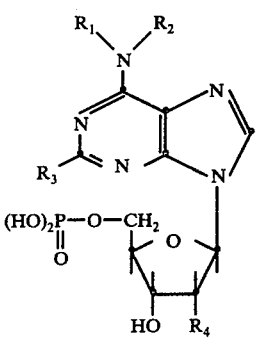

(Ia)

wherein $R_1$, $R_2$ and $R_3$ have the values given above and $R_4$ is H or OH.

When two hydroxy groups of the same molecule are blocked by a single phosphoric acid ester group, a cyclic monophosphate, e.g., of general Formula IV, is produced:

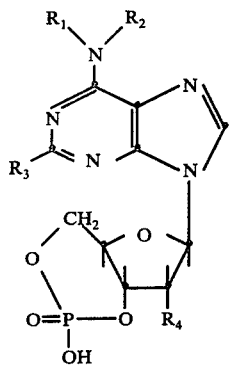

(IV)

wherein $R_1$, $R_2$ and $R_3$ have the values given above and $R_4$ is H or OH.

When a hydroxy group of two different molecules are blocked by a single bridging phosphoric acid ester group, the product is a di- or polynucleotide, bridged at the 3-position or at the 3,5-position, respectively, e.g., of general Formula V:

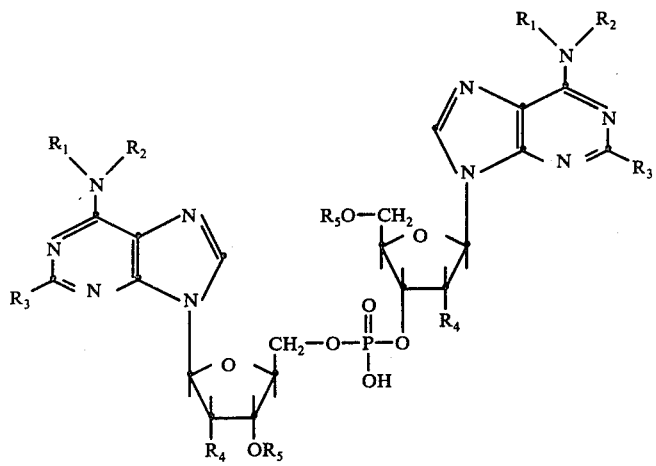

(V)

wherein $R_1$, $R_2$ and $R_3$ have the values given above, $R_4$ is H or OH, and $R_5$ is H or a like group of Formula I wherein Z is a ribofuranosyl or deoxyribofuranosyl group joined at a hydroxy group thereof by the bridging —P(OH)(O)— group.

Especially suitable as the sugar moieties are those of ribose and deoxyribose.

The compounds of Formula I wherein Z is a free sugar radical are, for the most part, known. The products of this invention of Formulae Ia, IV and V, like the corresponding compounds of Formula I wherein Z is a free sugar radical, possess advantageous biological activity, including antiproliferative activity and have beneficial effects on the cardiovascular system.

According to G. A. Le Page et al., Cancer Research 32, 2441 (1972) the 5'-phosphates or their salts are water soluble and thus easily applicable but have biological effects very much like the free substituted adenosines since they are readily cleaved by the phosphatases especially in the kidney to give the free substituted adenosines.

It is unnecessary to isolate the silylated compounds of general Formula II in the process of this invention. The 6-trialkyl-silyloxyadenosine nucleotides formed in situ can be directly reacted in the reaction solution with ammonia or an amine to obtain the corresponding adenosine nucleotides.

The type of reaction depends on the selected compound of the formula $HNR_1R_2$ and the catalyst. The treatment of the silyl compound of general Formula II with primary or secondary amines preferably is conducted at 0°–180° C. When using a salt of primary and secondary amines, the amine salt serves simultaneously as the reaction catalyst.

Examples of primary amines are alkylamines, e.g., methylamine, ethylamine, propylamine and butylamine, arylamines, e.g. aniline, and p-anisidine, aralkylamines, e.g., benzylamine, homoveratrylamine, tryptamine, 5-methoxy-tryptamine, N,N-dimethylethylenediamine and dopamine hydrochloride.

Examples of preferred secondary amines are dialkylamines, e.g., dimethylamine, diethylamine, heterocyclic amines, e.g., pyrrolidine, piperidine, morpholine, hexamethylenimine, N-methylpiperazine, N-(2-hydroxyethyl)-piperazine.

The reaction with the silylating agent and the primary or secondary amine can be conducted simultaneously.

The reaction with ammonia is effected under increased $NH_3$-pressure of about 20–50, preferably 25–35, atmospheres gauge. After 20–80 hours at 0°–180° C.; the reaction is usually complete. In the case of silylation with hexamethyldisilazane, wherein ammonia is liberated, the silylation and the reaction with ammonia can be accomplished in one stage.

An especially advantageous solvent for the reaction is excess amine of the formula $HNR_1R_2$. However, it is also possible to use an inert solvent, such as, for example, toluene, xylene, anisole, dioxane, glyme, pyridine, or, for the less soluble silyl compounds, preferably dimethylformamide or sulfolane.

Suitable catalysts are Lewis acids, especially metallic oxides, metallic salts and salts of amines. The metallic salts are optionally used in the reaction with excess amine of the formula $HNR_1R_2$.

The catalysts are employed in amounts of 0.001 mole to 5 moles, based on the nucleotide, but preferably in amounts of 0.05 - 1 mole. The most effective and preferred catalysts are acidic aluminum oxide, mercury(II) chloride, mercury(II) acetate, as well as zinc(II) chloride, tin(IV) chloride, titanium(IV) chloride, and boron trifluoride etherate, which are used in combination with excess amine; and salts of amines, such as, for example, ammonium sulfate, tryptamine hydrochloride, dopamine hydrochloride, pyridinium chloride, etc.

It is surprising that the phosphoric acid ester linkage is not cleaved during the reaction with amines at temperatures of up to 180° C.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

$N^6$-Benzyladenosine-5'-monophosphoric Acid

A suspension of 117.65 g. (0.3 mole) of the disodium salt of inosine-5'-monophosphoric acid in 188.7 ml. (0.9 mole) of hexamethyldisilazane and 113.7 ml. (0.9 mole) of trimethylchlorosilane was heated under reflux for 12 hours at a bath temperature of 145° C. Thereafter, the suspension was combined with 200 ml. of 1,2-dichloroethane (absolute) and filtered with the exclusion of moisture. The residue obtained after evaporation of the filtrate was stirred after the addition of 62.9 ml. (0.3 mole) of hexamethyldisilazane, 163.7 ml. (1.5 mole) of benzylamine and 3.96 g. (0.03 mole) of ammonium sulfate, for 27 hours at a bath temperature of 145° C. The thus-produced hexamethyldisiloxane (b.p. 101° C.) was distilled off through a Vigreux column (10 cm.). The brown reaction mixture was combined with 600 ml. of methanol and agitated at room temperature for 16 hours. The thus-precipitated benzylamine salt of $N^6$-benzyladenosine-5'-monophosphoric acid was filtered off, washed with ethanol, and dried. After crystallization of the concentrated filtrate from ethanol, filtering off the reaction product, and drying of the crystals, the yield was 146.8 g. of benzylamine salt. By ion exchange chromatography in water via a "DOWEX" column (type 50 WX2, H+ form; 2.5 × 120 cm.), concentration of the fractions, and crystallization from ethanol/water, the yield was 93.5 g. (71%) of colorless-crystalline $N^6$-benzyladenosine-5'-monophosphoric acid, m.p. 173° - 175° C.

EXAMPLE 2

$N^6$-[2-(5-Methoxy-3-indolyl-)ethyl]-adenosine-5'-monophosphoric Acid, Trihydrate 11.765 g (30 millimoles) of the disodium salt of inosine-5'-monophosphoric acid was boiled under reflux in 18.87 ml (90 millimoles) hexamethyldisilazane and 11.35 ml (90 millimoles) trimethylchlorosilane at 145° C bath temperature for 12 hours. After cooling the undissolved substance was filtered off in an argon atmosphere under addition of 100 ml 1,2 dichloroethane (absolute). The remaining oily residue was mixed with 5.24 ml (25 millimoles) hexamethyldisilazane, 9.51 g (50 millimoles) 5-methoxy-tryptamine and 0.446 g (0.25 millimoles) p-toluenesulfonic acid (monohydrate), then stirred at 145° - 150° C bath temperature for 20 hours while simultaneously distilling off (5 cm Vigreux column, Kp→98°). The reaction solution was heated in 200 ml $CH_3OH$ for 3 hours and then evaporated. The residue was mixed with a 300 ml $Na_2CO_3$-solution and three times extracted, each time with 200 ml methylene chlorine. The $Na_2CO_3$ phase was evaporated 5 times with 200 ml $CH_3OH$ each time and the dry residue was extracted. After evaporation of the methanol the remaining residue was dissolved in 100 ml water (pH 9) and acidified with diluted hydrochloric acid (pH 2) thus obtaining a light brown substance. The precipitate was filtered off and crystallized from water. Yield: 8.2 g 57.1% of $N^6$-[2-(5-methoxy-3-indolyl)-ethyl]-adenosine-5'-monophosphoric acid, trihydrate (m.p. = 161° - 165° C).

EXAMPLE 3

$N^6.N^6$-[N-(2-hydroxyethyl)-3-aza-pentamethylene]-adenosine-5'-monophosphoric acid, Monohydrate.

39.22 g (100 millimoles) of disodium salt of inosine-5'-monophosphoric acid was suspended in 62,72 ml (300 millimoles) hexamethyldisilazane and 37,89 ml (300 millimoles) trimethylchlorsilane, thereafter boiled under reflux at 145° C bath temperature for 10 hours.

After cooling off and addition of 150 ml 1,2-dichloroethane (absolute) the dark brown opaque solution was filtered off in an argon atmosphere and evaporated in vacuum. The oily residue was given to 40.9 ml (195 millimoles) hexamethyldisilazane, 25.8 ml (210 millimoles) N-(2-hydroxyethyl)-piperazine and 1.902 g (10 millimoles) p-toluene sulfonic acid (monohydrate) and subsequently stirred at 145° - 150° C bath temperature for 14 hours while simultaneously distilling off (5 cm Vigreux column, Kp→98°). The reaction solution was heated in 500 ml $CH_3OH$ at 100° C for 4 hours and thereafter evaporated.

The remaining residue was dissolved in 600 ml water and chromatographed via a 300 ml "DOWEX" column (type 50 MX2, H+ form). After evaporation and crystallization from $CH_3OH/H_2O$ the samples 3 - 20 (600 ml water each) yielded 34.2 g 71.5% $N^6.N^6$-[N-(2-hydroxyethyl)-3-aza-pentamethylene]-adenosine-5'-monophosphoric acid, monohydrate (m.p. 203° - 206° C).

EXAMPLE 4

$N^6$-Benzyl-2-aminoadenosine-5'-monophosphoric acid, Monohydrate 40.72 g (100 millimoles) of disodium salt of guanosine-5'-monophosphoric acid was suspended in 62.72 ml (300 millimoles) hexamethyldisilazane, 37.89 ml (300 millimoles) trimethylchlorosilane and 80 ml pyridine (absolute) heated at 145° C bath temperature for 72 hours. The soluble substance was filtered off in an argon atmosphere, washed with pyridine and the filtrate evaporated in vacuum. The residue was given to 20.91 ml (100 millimoles) hexamethyldisilazane, 54.56 ml (500 millimoles) benzylamine, and 1.32 g (10 millimoles) ammonium sulfate. This was stirred at 145° C bath temperature for 18 hours while simultaneously distilling off hexamethyldisilazane (boiling point→98° C, 6cm Vigreux-column).

After adding 500 ml methanol and boiling for one hour evaporation was started and the sticky brown residue was suspended three times with 600 ml ether each time and the obtained crystalline substance filtered off. After dissolving in methanol/water the hydrochloric acid was acidified until pH 2, after treating with carbon it was evaporated and crystallized from water, m.p. 229° - 232° C. Yield: 39.8 g (88%), (84.6% as Monohydrate).

Following the above procedure, the disodium salt of guanosine-5'-monophosphoric acid is converted to $N^6$-benzyl-2-amino-adenosine-5'-monophosphoric acid. Similarly, by substituting a molar equivalent amount of pyrrolidine, piperidine, aniline, phenethylamine, 3,4-dimethoxyphenethylamine, N-methylpiperazine, piperidine and morpholine for the benzylamine in these reactions, there is produced, respectively, employing the disodium salt of inosine-5-monophosphoric acid, $N^6,N^6$-tetramethylene-adenosine-5'-monophosphoric acid,
$N^6,N^6$-pentamethylene-adenosine-5'-monophosphoric acid,
$N^6$-phenyl-adenosine-5'-monophosphoric acid,
$N^6$-$\beta$-phenethyl-adenosine-5'-monophosphoric acid,
$N^6$-3,4-dimethoxy-$\beta$-phenethyl-adenosine-5'-monophosphoric acid.
6-(4-N-methyl-piperazino)-9-$\beta$-D-ribofuranosyl-purine-5'-monophosphoric acid,
6-piperidino-9-$\beta$-D-ribofuranosyl-purine-5'-monophosphoric acid,
6-morpholino-9-$\beta$-D-ribofuranosyl-purine-5'-monophosphoric acid,
and when employing the disodium salt of guanosine-5-monophosphoric acid,
$N^6,N^6$-tetramethylene-2-amino-adenosine-5'-monophosphoric acid,
$N^6,N^6$-pentamethylene-2-amino-adenosine-5'-monophosphoric acid,
$N^6$-phenyl-2-amino-adenosine-5'-monophosphoric acid,
$N^6$-$\beta$-phenethyl-2-amino-adenosine-5'-monophosphoric acid,
$N^6$-3,4-dimethoxy-$\beta$-phenethyl-2-amino-adenosine-5'-monophosphoric acid,
6-(4-N-methyl-piperazino)-2-amino-9-$\beta$-D-ribofuranosyl-purine-5'-monophosphoric acid,
6-piperidino-2-amino-9-$\beta$-D-ribofuranosyl-purine-5'-monophosphoric acid, and
6-morpholino-2-amino-9-$\beta$-D-ribofuranosyl-purine-5'-monophosphoric acid.

Similarly, by substituting the 2'-deoxy-ribosides corresponding to the disodium salts of ionosine-5'-monophosphoric acid and guanosine-5'-monophosphoric acids, there are produced $N^6$-benzyl-2'-deoxy-adenosine-5'-monophosphoric acid and $N^6$-benzyl-2-amino-2'-deoxy-adenosine-5'-monophosphoric acid.

The monosodium salts of inosine- and guanosine-3',5'-cyclophosphate are converted to $N^6$-benzyl-adenosine-3',5'-cyclophosphate and $N^6$-benzyl-2-amino-adenosine-3',5'-cyclophosphate, respectively.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of $N^6$-substituted adenosines of the formula wherein $R_1$ and $R_2$ each are a hydrogen atom or alkyl of 1 to 6 carbon atoms, monocyclic carbocyclic aralkyl or aryl of up to 10 carbon atoms which is unsubstituted or substituted by hydroxy or alkoxy of 1 to 4 carbon atoms, a heterocyclic ring of 4 to 7 ring members and containing a total of 1 to 3 nitrogen atoms or an oxygen or sulfur atom, or $R_1$ is a hydrogen atom and $R_2$ is hydroxy, amino or terminally substituted alkyl, or $R_1$ and $R_2$ collectively with the N-atom are a heterocyclic ring as defined hereinabove; $R_3$ is a hydrogen atom or amino; and Z is a ribofuranosyl or deoxyribofuranosyl moiety at least one of whose hydroxy groups is esterified with a phosphoric acid ester group, which comprises reacting a 6-trialkyl-silyloxypurine of the formula wherein $R'_3$ is a hydrogen atom or —$NSi(Alkyl)_3$, Z' is a silylated phosphoric acid acylated ribofuranosyl or deoxyribofuranosyl moiety, with ammonia or with an amine of the formula $HNR_1R_2$ or an acid addition salt thereof, wherein $R_1$ and $R_2$ have the values given above, alkyl in each instance being the same alkyl of 1 to 4 carbon atoms.

2. A process according to claim 1 wherein alkyl is methyl.

3. A process according to claim 1 wherein $R'_3$ is a hydrogen atom.

4. A process according to claim 1 wherein Z' is $\beta$-D-ribofuranosyl whose primary hydroxy group is esterified with a monophosphoric acid ester group and whose free hydroxy groups are silylated with —$Si(Alkyl)_3$ groups.

5. A process according to claim 1 wherein the starting 6-trialkyl-silyloxypurine is reacted with a primary amine.

6. A process according to claim 5 wherein the primary amine is benzylamine.

7. A process according to claim 5 wherein the reaction is conducted in the presence of a Lewis Acid as reaction catalyst.

8. A process according to claim 1 wherein Z' is β-D-ribofuranosyl whose primary hydroxy group is esterified with a monophosphoric acid ester group and whose free hydroxy groups are silylated with —Si(Alkyl)$_3$ groups, wherein the starting 6-trialkyl-silyloxypurine is reacted with a primary amine, and wherein the primary amine is benzylamine.

9. A process according to claim 8 wherein Alkyl is methyl.

10. A compound of the formula

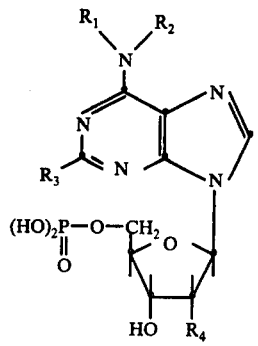

wherein $R_1$ and $R_2$ each are alkyl of 1 to 6 carbon atoms, monocyclic carbocyclic aralkyl or aryl of up to 10 carbon atoms which is unsubstituted or substituted by hydroxy or alkoxy of 1 to 4 carbon atoms, a heterocyclic ring of 4 to 7 ring members and containing a total of 1 to 3 nitrogen atoms or an oxygen or sulfur atom, or $R_1$ is a hydrogen atom and $R_2$ is as defined above or is hydroxy, amino or terminally substituted alkyl, or $R_1$ and $R_2$ collectively with the N-atom are a heterocyclic ring as defined hereinabove; $R_3$ is H or $NH_2$; and $R_4$ is H or OH.

11. A compound of claim 10, $N^6$-benzyl-2-aminoadenosine-5'-monophosphoric acid.

12. A compound of claim 10, $N^6$-[2-(5-Methoxy-3-indolyl)-ethyl]-adenosine-5'-monophosphoric Acid, Trihydrate.

13. A compound of claim 10, $N^6.N^6$-[N-(2-hydroxyethyl)-3-aza-pentamethylene]-adenosine-5'-monophosphoric Acid, Monohydrate.

* * * * *